United States Patent [19]

Bradshaw et al.

[11] Patent Number: 4,909,935

[45] Date of Patent: Mar. 20, 1990

[54] CHROMATOGRAPHIC ARYLCARBOXAMIDE POLYSILOXANES

[75] Inventors: Jerald S. Bradshaw, Provo; Milton L. Lee, Pleasant Grove; Karin Markides, Springville, all of Utah

[73] Assignee: Brigham Young University, Provo, Utah

[21] Appl. No.: 202,714

[22] Filed: Jun. 3, 1988

[51] Int. Cl.$^4$ ............................................. B01D 15/08
[52] U.S. Cl. ............................ 210/198.2; 210/502.1; 210/656; 528/15; 528/23; 528/25; 528/42; 528/43; 556/450
[58] Field of Search ................ 556/450; 528/15, 23, 528/25, 42, 43; 570/126; 210/656, 198.2, 502.1; 55/386

[56] References Cited

U.S. PATENT DOCUMENTS 4,745,169 5/1988 Sugiyama ......................... 556/450

OTHER PUBLICATIONS

Frank, "Rapid Gas–Chromatographic Separation of Amino–Acid Enantiomers with a Novel Chiral Stationary Phase", Journal of Chromatographic Science, 1977, vol. 15, pp. 174–179.
Richter, "Nonextractable Cyanopropyl Polysiloxane Stationary Phases for Capillary Chromatography," Chromatographia, 1983, vol. 17, pp. 570–573.
Kuei, N–Octylmethyl polysiloxane stationary phases for capillary gas and supercritical fluid chromatography Chromatographia, 1985, vol. 20, pp. 25–30.
Junes, "Synthesis at Smectic Liquid–Crystalline Polysiloxanes from Biphenyl Carboxylate Esters", Journal of Organic Chemistry, 1984, vol. 49, pp. 4947–4951.
W. A. Konig, "Separation of Enantiomers by Capillary Gas Chromatography with Chiral Stationary Phases" Journal of High Resolution Chromatography and Chromatography Communication, 1982, vol. 5, pp. 588–595.
Liu, "Chiral Stationary Phases for the Gas–Liquid Chromatographic Separation of Enantiomers" Journal of Chromatography, 1983, vol. 271, pp. 309–323.
Koppenhoefer, "Chiral Recognition in Gas Chromatographic Analysis of Enantiomers on Chiral Polysiloxanes," Journal of Chromatography Library, 1985, vol. 32 pp. 1–42.
Roder, Chiral SFC–Separations Using Polymer Coated Open Tubular Fused Silica Columns, Journal of High Resolution Chromatography and Chromatography Communications 1987, vol. 10, pp. 665–667.

Primary Examiner—Ernest G. Therkorn

[57] ABSTRACT

Chiral arylcarboxamide-containing alkenes and alkoxysilanes and polysiloxane polymers containing chiral arylcarboxamide-substituted side chains and methods for their preparation are disclosed. The chiral arylcarboxamide-containing alkenes are used to prepare the chiral arylcarboxamide-containing polysiloxane polymers which are useful as stationary phase coatings in gas-liquid and supercritical fluid chromatography in the separation and analysis of enantiomeric and other stereoisomeric mixtures of various substances. The chiral arylcarboxamide containing alkoxysilanes are reactive towards silica particles for use as packing in liquid chromatography columns.

15 Claims, 5 Drawing Sheets

CHROMATOGRAPHIC ARYLCARBOXAMIDE POLYSILOXANES

FIELD OF INVENTION

The present invention relates to novel chiral arylcarboxamide-containing alkenes, alkoxy silanes, and polysiloxanes, and the use of the polysiloxanes as capillary column stationary phases in gas-liquid and supercritical fluid chromatographic separations, and analyses of enantiomeric and other stereoisomeric mixtures of various substances, and the use of silica-bound chiral arylcarboxamide-containing materials, prepared by coating and heating the chiral arylcarboxamide-containing alkoxy silanes on silica, in solid supported supercritical fluid chromatography and liquid chromatography separations, and analyses of enantiomeric and other stereoisomeric mixtures of various structures.

THE PRIOR ART

Many different chiral materials have been used as stationary phases in gas and liquid chromatography to separate enantiomeric and other stereoisomeric mixtures of various substances. Three general references which discuss chiral phases and their uses are as follows:
(1) W. A. König in SEPARATION OF ENANTIOMERS BY CAPILLARY GAS CHROMATOGRAPHY WITH CHIRAL STATIONARY PHASES, Journal of High Resolution Chromatography & Chromatography Communications, 1982, vol. 5, 588-595. (2) R. H. Liu and Warren W. Ku in CHIRAL STATIONARY PHASES FOR THE GAS-LIQUID CHROMATOGRAPHIC SEPARATION OF ENANTIOMERS, Journal of Chromatography, 1983, vol. 271, 309-323. And (3) B. Koppenhoefer and E. Beyer in CHIRAL RECOGNITION IN GAS CHROMATOGRAPHIC ANALYSIS OF ENANTIOMERS ON CHIRAL POLYSILOXANES, Journal of Chromatography Library, 1985, vol. 32, 1-42. One recent paper describes the use of a chiral phase in supercritical fluid chromatographic separations in W. Roder, F. J. Ruffing, G. Schomburg and W. H. Pirkle, CHIRAL SFC-SEPARATIONS USING POLYMER-COATED OPEN TUBULAR FUSED SILICA COLUMNS. COMPARISON OF ENANTIOMERIC SELECTIVITY IN SFC AND LC USING THE SAME STATIONARY PHASE OF THE PIRKLE TYPE, Journal of High Resolution Chromatography and Chromatography Communications, 1987, vol. 10, 665-667.

Nearly all of the previously used chiral phases are low molecular weight materials which cannot be used successfully in capillary columns for high temperature gas or supercritical fluid chromatography because of their low thermal stabilities and because they are soluble in supercritical fluids. This would include a number of chiral amino esters, dipeptides, diamides and related materials which are discussed in the three reviews mentioned above. Some of these chiral materials have been bonded to silica gel for use in liquid chromatographic separations.

H. Frank, G. J. Nicholson and E. Bayer in RAPID GAS-CHROMATOGRAPHIC SEPARATION OF AMINO-ACID ENANTIOMERS WITH A NOVEL CHIRAL STATIONARY PHASE, Journal of Chromatographic Science, 1977, vol. 15, 174-179 report the development of a polysiloxane material containing L-valine-tert-butylamide side chains which has the ability to be used at temperatures up to 220° C. The material, called Chirasil-val TM, is now commerically available. The three reviews mentioned above describe the uses of Chirasil-val TM and other similar polysiloxane-containing L-valine-(S)-α-phenylethylamide side chains. The commercial Chirasil-val TM phases are often not reproducible in their separation properties. Also considerable column bleeding is observed at temperatures above 210° C. Another major problem with the polysiloxane materials mentioned here is that their structure has the chiral C—H group next to a carbonyl function (C=O). These types of materials would racemize at high temperatures, and the resulting chiral material would no longer separate enantiomeric mixtures.

Thus, it will be recognized that what is needed (in the art) is a chromatographic phase or phases that will separate enantiomeric and other stereoisomeric substances, that will have both low and high operating temperatures and that can be immobilized on a capillary column so that supercritical fluids will not strip or wash the phase off the columns. Similar phases which are stable to all types of solvents and can be bound onto silica particles for liquid chromatography (LC) columns would also be an important addition to LC technology. Chromatographic phases having these novel properties for separating enantiomeric substances are disclosed and claimed in the present invention.

BRIEF SUMMARY AND OBJECTIVES OF THE INVENTION

The present invention relates to chiral arylcarboxamide-containing alkenes having the following formula:

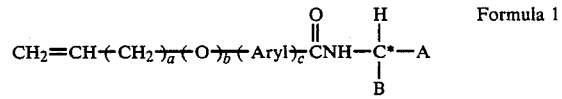

Formula 1

In the above formula 1, a is an integer from 0 to about 12; b is 0 or 1; c is 1 or 2; Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group (—CO$_2$R$^1$) where R$^1$ is any alkyl of 1 to 22 carbons or phenyl, naphthyl or biphenyl; any mono- or disubstituted carboxamide group [C(O)NR$^2$R$^3$] where R$^2$ is any alkyl of 1 to 22 carbons or phenyl, naphthyl or biphenyl, or any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and R$^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral.

The present invention also relates to chiral arylcarboxamide-containing mono-, di- or trialkoxysilanes having the following general formula:

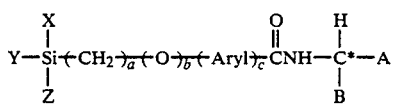

Formula 2

In the above formula 2, a is an integer from 2 to about 14; b is 0 or 1; c is 1 or 2; Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group, ($-CO_2R^1$) where $R^1$ is any alkyl of 1 to 22 carbons or phenyl, naphthyl, or biphenyl; any mono- or disubstituted carboxamide group [$C(O)NR^2R^3$] where $R^2$ is any alkyl of 1 to 22 carbons or phenyl, naphthyl, or biphenyl, or any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and $R^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral.

The present invention also relates to polymers comprising a polysiloxane backbone to which are attached the chiral arylcarboxamide-containing side chains formulated in accordance to Formula 1. Such polymers thus having the following general formula:

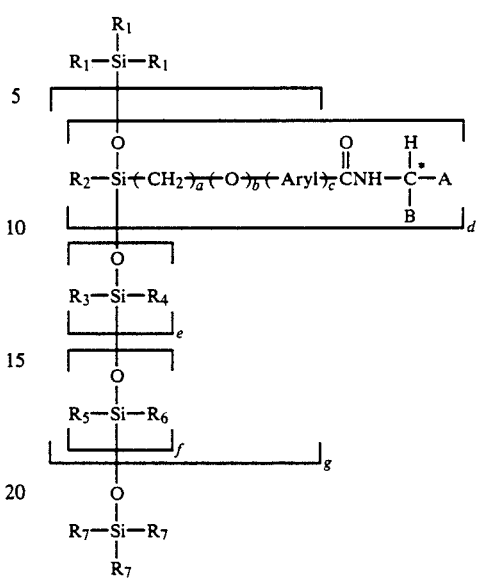

Formula 3

In the above formula 3, a is an integer from 2 to about 14; b is 0 or 1; c is 1 or 2; d is an integer from 1 to about 14; e is an integer from 10 to about 40; f is an integer from 0 to about 1; g is an integer from 3 to about 100.

Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group ($CO_2R^1$) where $R^1$ is any alkyl of 1 to 22 carbons or phenyl, naphthyl or biphenyl; any mono- or disubstituted carboxamide group [$C(O)NR^2R^3$] where $R^2$ is any alkyl of 1 to 22 carbons or phenyl, naphthyl or biphenyl, any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and $R^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral.

$R_1$ and $R_7$ are selected from the group consisting of lower alkyl, lower alkenyl, lower haloalkyl and phenyl; $R_2$, $R_3$, $R_4$ and $R_5$ are members selected from the group consisting of hydrogen, lower alkyl, phenyl substituted lower alkyl, lower alkyl substituted phenyl, lower alkoxy substituted phenyl and halosubstituted phenyl.

$R_6$ is a member selected from the group consisting of alkyl of 1 to 12 carbon atoms, alkenyl of 2 to 8 carbon atoms, phenyl substituted lower alkyl and lower alkyl substituted phenyl. The essence of the $R_6$ group is that it is functional to react with a free radical source to facilitate crosslinking of two or more polysiloxane backbones.

Depending upon the starting materials, the polymer elements d, e, and f used to form the polymer chain will be ordered in a statistically governed sequence. The specific sequence will have little or no effect on the functionality of the polymer. The ratios of d, e, and f will be such that about 5–20% of the silane atoms will contain a chiral amide substituent.

As noted in the above formula 3, the chiral amide group of the present invention is attached to a polysiloxane backbone through a stable hydrocarbon or ether-hydrocarbon linkage composed of oligomethyleneoxyaryl or oligomethylenearyl groups depending upon the values of a and b. The aryl group is a very stable part of the molecule. The polysiloxane backbone is crosslinked to one or more other polysiloxane chains to immobilize the material and provide higher thermal stability in gas chromatography and resistance to washout of the phase in supercritical fluid chromatography. As also will be recognized, when the chiral carbon is not next to a carbonyl group (where A is any of the indicated groups except carboxyl or carboxyamide), the material will be stable to racemization at temperatures up to about 300° C.

The chiral arylcarboxamide-containing alkene of formula 1 is converted to mono-, di- or trialkoxysilane as shown in formula 2, which alkoxysilane is reactive towards silica particles, thus, allowing the attachment of the chiral amide group to silica particles for use in LC or SFC. It should be noted that the a values in formulas 1 and 2 are not necessarily the same.

There is a need for the development of stationary phases capable of separating chiral and other stereoisomeric compounds in high temperature capillary gas and in supercritical fluid chromatography. A number of peptide materials have been used successfully for the gas chromatographic separation of enantiomers at moderate temperatures as reported in the above mentioned review papers. The three reviews also mention work on the use of di-and tripeptides as well as various chiral amides which were not attached to a polysiloxane backbone.

The phases mentioned in the previous paragraph have the disadvantage that they must be used at moderate temperatures so that the materials will not bleed off the column. This problem has been partially solved by covalently bonding the amide type materials onto siloxane polymers. The Chirasil-Val ™ stationary phase material mentioned above and reviewed in the three reviews is a result of this development. These phases are capable of the separation of chiral compounds up to about 230° C. Recent advances in capillary chromatography have utilized a free radical process to crosslink polysiloxane chains and thus immobilize the phase in the capillary as reported by B. E. Richter and coworkers in NONEXTRACTABLE CYANOPROPYL POLYSILOXANE STATIONARY PHASES FOR CAPILLARY CHROMATOGRAPHY, Chromatographia, 1983, vol. 17, 570–573. These immobilized phase materials are not only useful in high temperature gas chromatography, but they can be used in supercritical fluid chromatography as shown by J. C. Kuei and coworkers in n-OCTYLMETHYLPOLYSILOXANE STATIONARY PHASES FOR CAPILLARY GAS AND SUPERCRITICAL FLUID CHROMATOGRAPHY, Chromatographia, 1985, vol 20, 25–30.

It is, therefore, an objective of the present invention to provide novel chiral arylcarboxamide-containing compounds and polymers.

It is also the objective of the present invention to provide new polysiloxane stationary phases with chiral arylcarboxamide-containing substituents which are usable at higher temperatures than the presently used chiral phases.

A further objective of the present invention is to provide a chiral arylcarboxamide-containing polysiloxane stationary phase which can be immobilized for use in capillary SFC with various mobile phases.

It is a further objective of this invention to provide phases containing chiral arylcarboxamide-substituents which exhibit good selectivity and good efficiency over a wide temperature range.

Another object of the present invention is to provide superior methods for separating the enantiomers and other stereoisomers of various chemical compounds from mixtures thereof using gas-liquid chromatography.

A further object of the present invention is to provide stationary phases which are capable of performing separations based on stereochemical properties of the solutes in addition to vapor pressure and other solute properties.

Yet another object of the present invention is to provide superior methods for separating the enantiomers and other stereoisomers of various chemical compounds from mixtures thereof using liquid chromatography.

These and other objects and features of the present invention will be more fully apparent from the following description and appended claims, taken in conjunction with the accompanying drawings.

DETAILED DESCRIPTION OF THE PREFERRED EMBODIMENTS

Chiral Arylcarboxamide-Containing Alkene Embodiments

Figure 1:
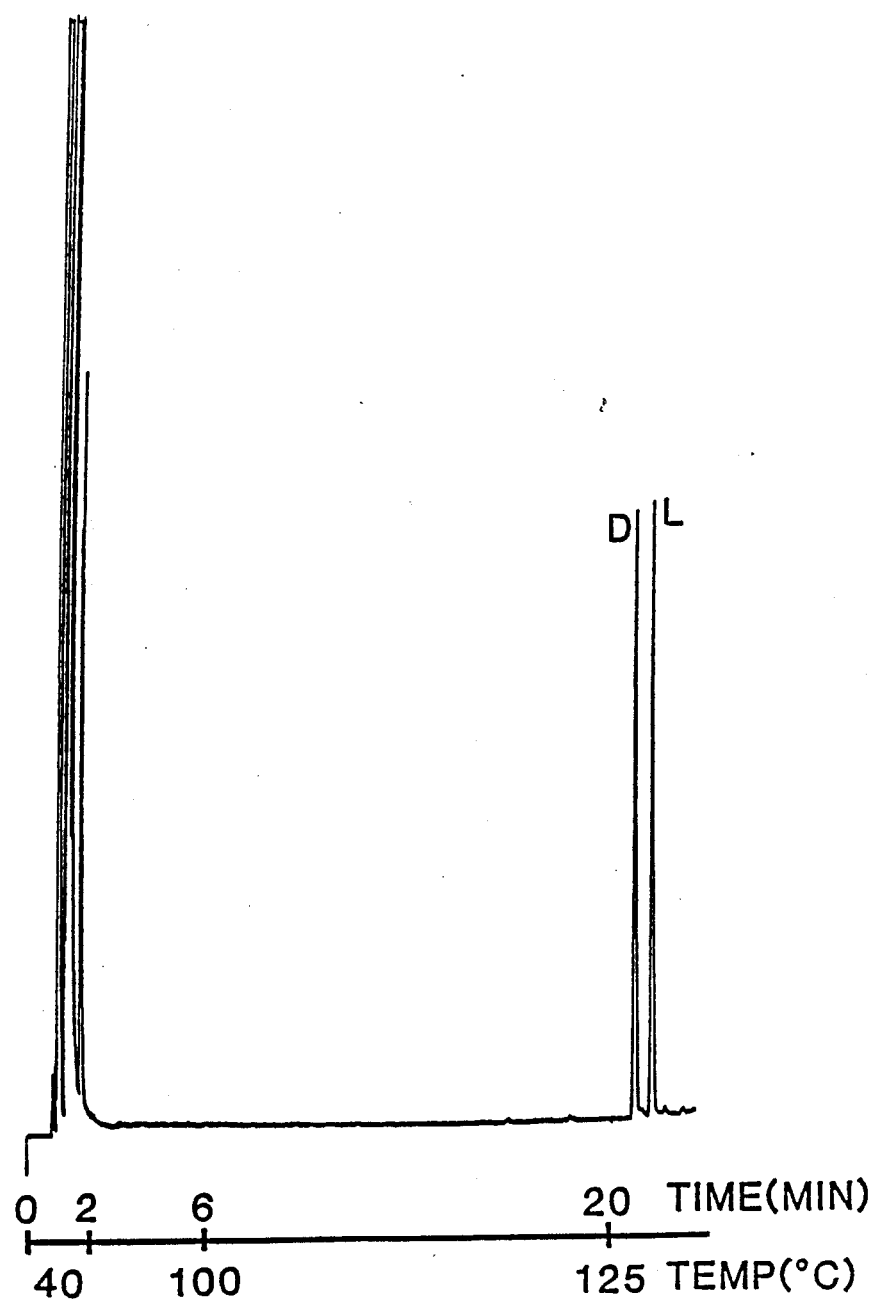
FIG. 1 illustrates a gas-liquid chromatogram, wherein derivatives of the D and L isomers of methionine were separated using a stationary phase in accordance with one embodiment of the present invention.

The present invention relates to novel chiral arylcarboxamide-containing alkenes, which are used to prepare chiral arylcarboxamide-containing alkoxysilanes and polysiloxanes. The chiral arylcarboxamide-containing polysiloxanes exhibit exceptional utility as stationary phases in the chromatographic separations of the enantiomers and other stereoisomers of various chemical substances. The chiral arylcarboxamide-containing alkoxysilanes are used to prepare packed supercritical fluid and liquid chromatographic and LC phases. The novel chiral arylcarboxamide-containing alkenes of the present invention have the following general formula:

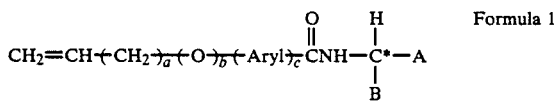

Formula 1

In Formula 1 above, a is 0 to about 12, with 0 and 1 being most preferred; b is 0 or 1, with 0 and 1 the most preferred; and c is 1 or 2, with 1 being preferred. In one particularly preferred embodiment a, b and c are all 1. In another embodiment, a and b are 0 and c is 1.

Further, in Formula 1, Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group ($-CO_2R^1$) where $R^1$ is any alkyl of 1 to 22 carbons or phenyl, naphthyl or biphenyl; any mono- or disubstituted carboxamide group [$C(O)NR^2R^3$] where $R^2$ is any alkyl of 1 to 22 carbons or phenyl, naphthyl or biphenyl or any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and $R^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral. In one particularly preferred embodiment, Aryl is phenyl, A is 1-naphthyl and B is methyl. A second embodiment has Aryl and A=phenyl and B=methyl. Another embodiment has Aryl=phenyl, A=isopropoxycarbonyl [$-CO_2CH(CH_3)_2$] and B=sec-butyl [$-CH(CH_3)CH_2CH_3$]. A fourth embodiment has Aryl=phenyl, A=4-methoxyphenoxycarbonyl [$-CO_2-4-C_6H_4OCH_3$] and B=methyl.

Further, it will be recognized that substitutions of any of the foregoing chemical groups for A or B or for hydrogen on the aryl group will be within the scope of this invention. By way of example only, substituting a halogen in one of these chemical groups would be considered to be within the scope of the present invention. Thus, all well known chemical substitutions or derivatives of the compounds of Formula 1 are to be considered within the scope of the present invention.

One presently preferred procedure in preparing compounds in accordance with Formula 1 where Aryl=phenyl and c=1 or 2 is given in Procedure I below.

PROCEDURE I

In this procedure, the appropriate alkenyloxy- (or alkenyl-) benzoic (or 4-phenylbenzoic) acid is first prepared according to the procedure mentioned by B. A. Jones and coworkers in SYNTHESIS OF SMECTIC LIQUID-CRYSTALLINE POLYSILOXANES FROM BIPHENYLCARBOXYLATE ESTERS AND THEIR USE AS STATIONARY PHASES FOR HIGH-RESOLUTION GAS CHROMATOGRAPHY, Journal of Organic Chemistry, 1984, vol 49, 4947–4951. This carboxylic acid is reacted successively with oxalyl chloride and then with the chiral amine as shown in Equation 1. In

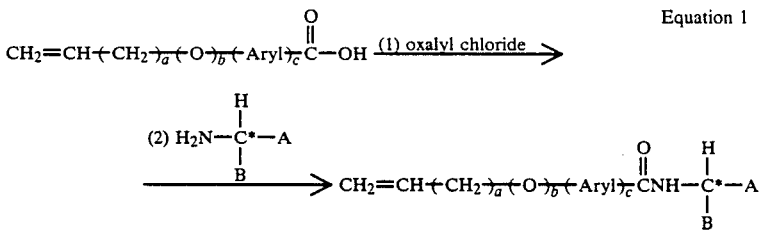

Equation 1, the desired alkenyloxyaromatic acid is reacted with oxalyl chloride and then the desired chiral amine to form the corresponding chiral arylcarboxamide-containing alkene in accordance with Formula 1. As will be appreciated, the values of a, b, and c and the nature of Aryl, A and B in Equation 1 will depend on the specific chiral arylcarboxamide to be made.

In order to achieve the reactions of Equation 1, the 4-alkenyloxybenzoic acid [or 4-(4-alkenyloxyphenyl)-benzoic acid] (where Aryl=phenyl) is dissolved into solution at room temperature in a mixture of about two or three equivalents of a chlorinating agent such as oxalyl chloride or thionyl chloride in an excess of an appropriate solvent such a methylene chloride or anhydrous tetrahydrofuran (THF) and a drop or two of dimethylformamide (DMF). This mixture is stirred at room temperature for 2 to 10 hours. The solvent and excess of chlorinating reagent are then evaporated under reduced pressure and 10 to 25 milliliters (ml) of benzene or toluene are added. These solvents are also removed under reduced pressure so that all remaining traces of the chlorinating reagent are removed. The resulting crude acid chloride is dissolved in an anhydrous, aprotic solvent (use about 25 mL of solvent per 0.01 mole of acid chloride) and the resulting solution is slowly added (through a dropping funnel) to an ice cold, stirring solution of the equivalent amount of the appropriate chiral amine in a mixture of 1 equivalent of triethylamine and the same aprotic solvent (use 50 mL of the solvent per 0.01 mole of amine). The chiral amines, such as 1-naphthyl-1-ethyl amine or an ester of an amino acid, can usually be purchased. The resulting mixture is stirred at 0° C. for 2 to 10 hours and at room temperature for an additional 2 to 5 hours. The resulting mixture is washed successively with 20 to 50 mL portions of 0.1M aqueous hydrochloric acid, dilute aqueous sodium bicarbonate and then with water until the water wash is neutral. The organic phase is dried using a drying agent such as anhydrous magnesium sulfate crystals, filtered and the solvent removed to give the crude, chiral amide. The chiral arylcarboxamide-containing alkene is recrystallized from an appropriate solvent such as ethanol.

It is understood that compounds corresponding to Formula 1 (a and b=0 and Aryl=phenyl) can be prepared in the same manner from 4-vinylbenzoic acid. Compounds of Formula 1 corresponding to a=2-10, b=1 and Aryl=phenyl can be prepared from 4-(ω-alkenyloxy)bromobenzene using a Grignard reaction and carbon dioxide. The 4-(ω-alkenyloxy)bromobenzene can be prepared from the reaction of 4-bromophenol, base and ω-bromo-1-alkene. The overall reaction is shown in Equation 2.

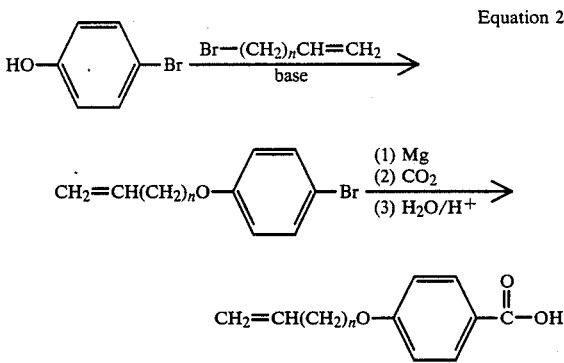

Equation 2

Compounds corresponding to Formula 1 (c=2) can be made from 4-(4-substituted phenyl)benzoic acid which in turn would be prepared as shown in Equation 2 except 4-(4-bromophenyl)phenol would be used instead of 4-bromophenol.

The following examples are given to illustrate compounds which have been made or may be made in accordance with Formula 1 of the present invention. These examples are illustrative only, and are not comprehensive of the many different compounds which have been or can be made within the scope of this invention.

EXAMPLE 1

In this example, a chiral arylcarboxamide-containing alkene was made wherein a=1, b=1, c=1, Aryl=phenyl, A=1-naphthyl ($-1-C_{10}H_7$) and B=methyl ($-CH_3$) in Formula 1.

4-Allyloxybenzoic acid (2.0 g, 0.011 mole) was stirred in a mixture of 3 equivalents of oxalyl chloride, 25 mL of anhydrous methylene chloride and one drop of dimethylformamide (DMF) at room temperature for 2 hours. The solvent and excess oxalyl chloride were removed under vacuum. Benzene (10 mL) was added and the material was again subjected to vacuum distillation to remove the remaining traces of oxalyl chloride. The remaining light yellow oil was dissolved in 25 mL of anhydrous methylene chloride, and the resulting solution was added dropwise to an ice cold, stirring solution of 2 g (0.012 mole) of (S)-1-(1-naphthyl)ethylamine (Aldrich) and 1 equivalent of triethylamine in 50 mL of anhydrous methylene chloride. The mixture was stirred at 0° C. for 2 h and at room temperature for 1 h. The resulting methylene chloride solution was washed successively with 0.1N aqueous hydrochloric acid, saturated aqueous sodium bicarbonate solution, and then with water. The phases were separated, and the aqueous phase was extracted twice with 50 mL portions of methylene chloride. The methylene chloride phases were combined, dried over anhydrous magnesium sulfate, and the solvent was removed to give (S)-N-1-(1-naphthyl)ethyl-4-allyloxybenzamide as a crude solid. The solid was recrystallized from absolute ethanol to give white crystals, 2.25 g (62%); mp 141°-143° C.; $[\alpha]_D^{25}$ +58.18° (c=0.373, CHCl$_3$); IR (KBr): 3220 and 1625 cm$^{-1}$; NMR (δ): 1.80 (3H, d, J=7.5 Hz), 4.56 (2H, d, J=5 Hz), 5.24–5.56 (2H, m,), 5.86–6.20 (2H, m), 6,36 (1H, q, J=6 Hz), 6.80–7.00 (2H, m); 7.40–8.28 (9H, m). Anal. for $C_{22}H_{21}NO_2$: Calcd: C, 79.75; H, 6.34, N, 4.22. Found: C, 79.62; H, 6.40; N, 4.44.

EXAMPLE 2

In this example, a chiral arylcarboxamide-containing alkene was made wherein a=1, b=1, c=1, Aryl=phenyl, A=phenyl ($-C_6H_5$) and B=methyl ($-CH_3$) in Formula 1.

The compound of this example [(S)-N-1-phenylethyl-4-allyloxybenzamide] was prepared in exactly the same manner as (S)-N-1-(1-naphthyl)ethyl-4-allyloxybenzamide in Example 1 except 2.5 g (0.014 mole) of (S)-1-phenylethylamine was used in Example 2 rather than 2 g (0.012 mole) of (S)-1-(1-naphthyl)ethylamine in Example 1. The (S)-N-1-phenylethyl-4-allyloxybenzamide product was isolated in a 67% yield; mp 147°-148° C.; $[\alpha]_D^{25}$ −12.62° (c=0.745, CHCl$_3$); IR (KBr): 3380 and 1640 cm$^{-1}$; NMR (δ): 1.64 (3H, d, J=7.4 Hz), 4.60 (2H, d, J=4.4 Hz), 5.28-5.52 (3H, m), 5.88–6.60 (2H, m), 6.92 (2H, d, J=8.9 Hz), 7.16-7.44 (5H, m), 7.76 (2H, d, J=8.9 Hz). Anal. for $C_{18}H_{19}NO_2$; Calcd: C, 76.87; H, 6.76; Found: C, 77.02; H, 6.82.

EXAMPLE 3

In this example, a chiral arylcarboxamide-containing alkene was made wherein a=1, b=1, c=1, Aryl=phenyl, A=isopropoxycarbonyl [$-CO_2CH(CH_3)_2$] and B=sec-butyl [$-CH(CH_3)CH_2CH_3$] in Formula 1.

(S)-Isopropyl isoleucinate was first prepared as follows. Isopropyl alcohol (400 mL) was cooled to −20° C. and 16.3 g (0.136 mole) of thionyl chloride was added with stirring, followed by 15 g (0.114 mole) of L-isoleucine. The solution was brought to room temperature and was further heated in an oil bath at reflux temperature under anhydrous conditions for 24 hours. Most of the solvent was then removed under reduced pressure. Anhydrous ether (100 mL) was added to the residue and the unreacted L-isoleucine hydrochloride was filtered and the solid was washed with ether. Ether was removed under reduced pressure and the residue was dissolved in 25 mL of dichloromethane. The dichloromethane solution was washed with saturated aqueous potassium carbonate. The organic material was dried over anhydrous magnesium sulfate and the solvent was removed at reduced pressure to give 8.8 g (44.5%) of the product as light yellow oil: $[\alpha]_D^{25}$ +20.86° (c=0.302, chloroform); IR (neat), 1720 cm$^{-1}$; NMR (δ) 0.84–1.08 (6H, m), 1.28 (6H, d, J=7.7 Hz), 1.08–1.40 (2H, m), 1.50 (2H, broad, disappeared in D$_2$O), 1.64–1.80 (1H, m), 3.32 (1H, d, J=6.1 Hz), 4.92–5.24 (1H, heptet). This material was used directly in the next step.

(S)-N-Isoleucyl-4-allyloxybenzamide isopropyl ester was prepared as in Example 1 except 2.6 g (0.015 mole) of 4-allyloxybenzoic acid and 2.5 g (0.014 mole) of (S)-isopropyl isoleucinate were used in Example 2 rather than the 2.0 g of 4-allyloxybenzoic acid and 2 g (S)-1-(1-naphthyl)ethylamine in Example 1. The product was recrystallized twice from petroleum ether (30°–60°) to give 2.1 g (37%) of (S)-N-isoleucyl-4-allyloxybenzamide isopropyl ester as a white crystalline solid; mp 48°–48.5° C.; $[\alpha]_D^{25}$ +48.93° (c=0.329, CHCl$_3$); IR (KBr): 3300, 1725 and 1625 cm$^{-1}$; NMR ($\delta$): 0.96–1.12 (6H, m), 1.36 (6H, d, J=7.2 Hz), 1.40–1.76 (2H, m), (1H, broad, signal disappeared in D$_2$O), 1.96–2.16 (1H, m,), 4.46 (2H, d, J=6.3 Hz), 4.74–5.20 (2H, m) 5.24–5.56 (2H, m) 5.88–6.28 (1H, m) 6.96 (2H, d, J=8.5 Hz), 7.80 (2H, d, J=8.5 Hz). Anal. for C$_{19}$H$_{27}$NO$_4$: Calcd: C, 68.47; H, 8.11; N, 4.20. Found: C, 68.50: H, 8.00; N, 4.30.

EXAMPLE 4

In this example, a chiral arylcarboxamide-containing alkene was prepared wherein a=1, b=1, c=1, Aryl=phenyl, A=4-methoxyphenoxycarbonyl (—CO$_2$—4—C$_6$H$_4$OCH$_3$), and B=methyl (—CH$_3$) in Formula 1.

4-Methoxyphenylalaninate was first prepared by reacting N-benzyloxycarbonyl-(S)-alanine (10.9 g, 0.049 mole) with 4-methoxyphenol and 1,3-dicyclohexylcarbodiimide to give 9.2 g (57%) of N-benzyloxycarbonyl-(S)-alanine 4-methoxyphenyl ester, mp 128°–129° C.; $[\alpha]_D^{25}$ −18.98° (c=0.769, CHCl$_3$); IR (KBr): 3320, 1750 and 1660 cm$^{-1}$; NMR ($\delta$): 1.52 (3H, d, J=7.4 Hz), 3.72 (3H, s), 4.48 (1H, q, J=7.4 Hz), 5.08 (2H, s), 5.36–5.48 (1H, broad, signal disappeared in D$_2$O), 6.68–7.48 (9H, m). Anal. for C$_{18}$H$_{19}$NO$_5$: Calcd: C, 65.65; H, 5,77; N, 4.25. Found: C, 65.74; H, 5.91; N, 4.31.

The benzylcarbonyl group was removed using hydrogen and 10% Pd/C to give a 57% yield of 4-methoxyphenyl-(S)-alaninate as white crystals; mp 162°–164° C.; $[\alpha]_D^{25}$ +3.91° (c=0.332, CH$_3$OH); IR (KBr): 3100, 3000 and 1760 cm$^{-1}$; NMR ($\delta$): 1.52 (3H, d, J=7.4 Hz), 2.32 (3H, s), 3,74 (3H, s), 4.08–4.32 (1H, q, J=7.4 Hz), 6.68–7.80 (8H, m), 8.16–8.44 (2H, broad, signal disappeared in D$_2$O). Anal. for C$_{17}$H$_{21}$NO$_6$S: Calcd: C, 55.58; H, 5.72; N, 3.81; Found: C, 55.43; H, 5.62; N, 3.83.

The 4-methoxyphenyl-(S)-alaninate (4.0 g, 0.011 mole) and 1.94 g (0.011 mole) of 4-allyloxybenzoic acid were reacted as in Example 1 except that 4-methoxyphenyl-(S)-alaninate was used in Example 4 rather than (S)-1-(1-naphthyl)ethylamine that was used in Example 1. The product (S)-N-alaninyl-4-allyloxybenzamide, 4-methoxyphenyl ester was recrystallized from absolute ethanol to give 2.0 g (52%) as white crystals; mp 160°–161° C.; $[\alpha]_D^{25}$ +14.38° (c=0.431, CHCl$_3$); IR(KBr); 3310, 1760 and 1640 cm$^{-1}$; NMR ($\delta$); 1.72 (3H, d, J=7.4 Hz), 3.82 (3H, s), 4.60 (2H, d, J=5.0 Hz), 5.04 (1H, q, J=7.4 Hz), 5.28–5.52 (2H, m), 5.92–6.26 (1H, m), 6.64–7.84 (9H, m). Anal. for C$_{20}$H$_{21}$NO$_5$: Calcd: C, 67.60; H, 5.91; N, 3.94. Found: C, 67.79; H, 5.90; N, 4.00.

EXAMPLE 5

In this example, a chiral arylcarboxamide-containing alkene was prepared wherein a=0, b=0, c=1, Aryl=phenyl, A=phenyl, (—C$_6$H$_5$), and B=methyl (—CH$_3$) in Formula 1.

(R)-N-α-Methylbenzyl-4-vinylbenzamide was prepared as above in Example 1 except 2.5 g (0.017 mole) of 4-vinylbenzoic acid and 2.13 g (0.018 mole) of (R)-α-methylbenzylamine (Aldrich) were used rather than the 2.0 g of 4-allyloxybenzoic acid and 2 g of (S)-1-(1-naphthyl)ethylamine in Example 1. The product was recrystallized from absolute ethanol to give 1.85 g (44%) of white crystals; mp 162°–163° C.; $[\alpha]_D^{25}$ −25.49° (c=0.404, CHCl$_3$); IR (KBr): 3390 and 1640 cm$^{-1}$; NMR ($\delta$): 1.64 (3H, d, J=7.4 Hz); 5.32 (1H, q, J=7.4 Hz); 5.44–5.94 (2H, m); 6.48–6.92 (2H, m), 7.24–7.82 (9H, m). Anal. for C$_{17}$H$_{17}$NO: Calcd: C, 81.27; H, 6.77. Found: C, 81.24; H, 6.79.

Chiral Arylcarboxamide-Containing Alkoxysilane Embodiments

The present invention also relates to novel chiral arylcarboxamide-containing mono-, di-, or trialkoxysilanes which exhibit utility for the coating of silica particles which are used in columns for packed column SFC and for liquid chromatography (LC). The novel chiral arylcarboxamide-containing compounds of the present invention have the following general formula.

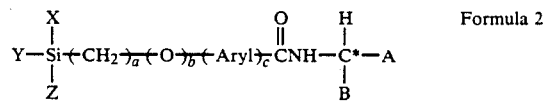

Formula 2

In Formula 2 above, a is 2 to about 14 with 2 and 3 being preferred; b is 0 or 1 with 0 or 1 being preferred; c is 1 or 2 with 1 being preferred.

Aryl is phenyl or napthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group (—CO$_2$R$^1$) where R$^1$ is any alkyl of 1 to 22 carbons or phenyl, naphthyl or biphenyl; any mono- or disubstituted carboxamide group [C(O)NR$^2$R$^3$] where R$^2$ is any alkyl of 1 to 22 carbons or phenyl, naphthyl or biphenyl, or any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and R$_3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral.

X is methoxy or ethoxy and Y and Z are methoxy, ethoxy, methyl, ethyl or halogenated substituents thereof.

It is to be understood that if X, Y and Z all are ethoxy, that the compound of Formula 2 will be a triethoxysilane. Likewise, a diethoxysilane would have X and Y as ethoxy groups and Z would be an alkyl or aryl group. One preferred embodiment has X and Y as ethoxy (—OCH$_2$CH$_3$) groups and Z as a methyl (—CH$_3$) group.

One presently preferred procedure for preparing compounds in accordance with Formula 2 is given in Procedure II below.

PROCEDURE II

In this procedure, a mixture of the chiral arylcarboxamide-containing alkene (prepared as shown in Procedure I) is reacted with a hydrosilane containing one, two or three alkoxy groups in an approximate 1 to 1 molar ratio, in accordance to Equation 3.

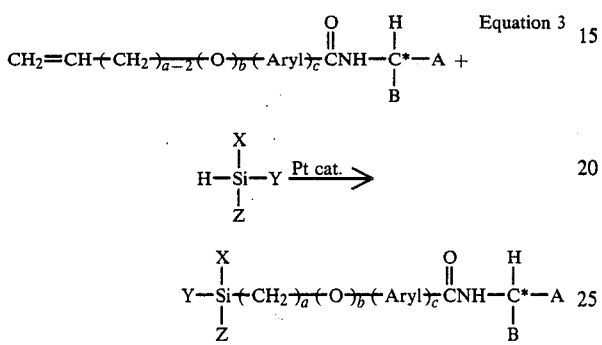

Equation 3

In order to achieve the reaction of Equation 3, a mixture of the chiral arylcarboxamide-containing alkene (prepared as described in Procedure I) and the hydrosilane (H—SiXYZ) are stirred at a temperature of between 70° C. and 90° C. for about 2 hr under an inert gas, such as argon, in a reflux condenser. A small amount of chloroplatinic acid is added and the mixture is refluxed for a period of between 10 and 24 hours. The product chiral arylcarboxamide-containing mono-, di-, or trialkoxysilane is purified usually by distillation. If the product is a solid, it can be purified by recrystallization using an appropriate non- proton-containing solvent such as benzene or hexane.

The following example is given to illustrate one compound which has been made in accordance with Formula 2. This example is exemplary only, and is not comprehensive of the many different compounds that can be made in accordance with this embodiment of the present invention.

EXAMPLE 6

In this example, a chiral arylcarboxamide-containing compound is prepared wherein a=3, b=1, c=1, Aryl=phenyl, A=1-naphthyl, B=methyl (—CH$_3$), X, Y and Z=ethoxy (—OCH$_2$CH$_3$) in Formula 2.

The chiral alkene arylcarboxamide of Example 1 (1.60 g, 5.0 mmol) was added to a slight excess of triethoxysilane (1.0 g) in 25 mL of toluene. The toluene had been purified by passing it through a charcoal column. The mixture was heated at 85° C. for 1 hour under an Argon atmosphere, then 30 μL of a catalyst composed of 1 part (by weight) of chloroplatinic acid, 1 part ethanol and 98 parts of tetrahydrofuran was added. The reaction mixture was stirred at 85° C. for about 24 hours when the IR spectrum of the mixture exhibited a small peak at 2160 cm$^{-1}$ indicating nearly all of the triethoxysilane had reacted. The solvent and excess triethoxysilane was removed by distillation under vacuum. The resulting solid (2.3 g, 93% yield) exhibited the following NMR spectrum: (δ) 0.6–0.8 (2H, t), 1.25 (9H, t), 1.60 (3H, d), 1.85 (2H, m), 3.70 (8H, m), 5.90 (1H, t), 6.70 (2H, d), 7.3–7.5 (5H, m), 7.6–7.8 (5H, m).

Chiral Arylcarboxamide-Containing Polysiloxane Polymer Embodiments

The present invention also relates to novel polymers containing chiral arylcarboxamide units which are formed by attaching the chiral arylcarboxamide-containing alkenes of Formula 1 to a polysiloxane backbone to form the polymers having the following general formula:

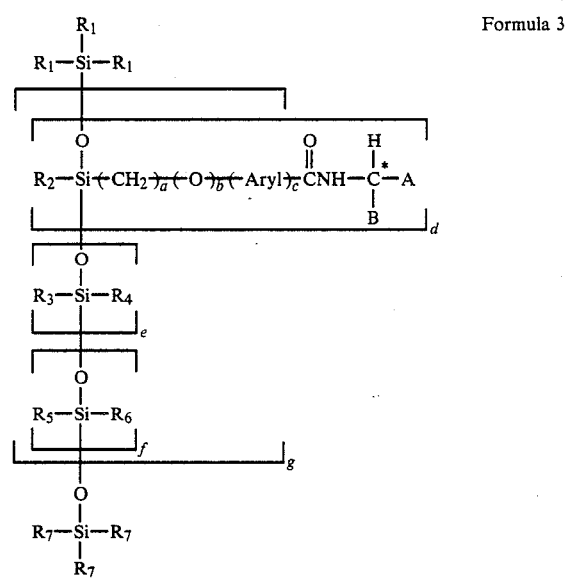

Formula 3

In Formula 3 above, a is 2 to about 14, with 2 and 3 being most preferred; b is 0 or 1, with 1 being preferred; c is 1 or 2, with 1 being preferred. Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group (—CO$_2$R$^1$) where R$^1$ is any alkyl of 1 to 22 carbons or phenyl, naphthyl or biphenyl; any mono- or disubstituted carboxamide group [C(O)NR$^2$R$^3$] where R$^2$ is any alkyl of 1 to 22 carbons or phenyl, naphthyl or biphenyl, or any alkyl ester of an amino acid unit such as alanine or phenylalanine (the nitrogen atom of the carboxamide group would be the nitrogen atom of the amine group of the amino acid alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing, and R$^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral. In one particularly preferred embodiment a=3, b=1, c=1, Aryl=phenyl, A=1-naphthyl and B=methyl. Another preferred embodiment has a=3, b=1, c=1, Aryl=phenyl, A=phenyl, and B=methyl.

Further in Formula 3, $R_1$ and $R_7$ are selected from the group consisting of lower alkyl, lower alkenyl, lower haloalkyl, and phenyl. The $R_1$ groups attached to the silyl atom may be the same or different as may the $R_7$ groups. Moreover $R_1$ and $R_7$ may be different. In one preferred embodiment, all $R_1$ and $R_7$ groups are methyl, i.e. forming trimethylsilyl radicals.

$R_2$, $R_3$, $R_4$, and $R_5$ are members selected from the group consisting of hydrogen, lower alkyl, phenyl, phenyl substituted lower alkyl, lower alkyl substituted phenyl, lower alkoxy substituted phenyl and halosubstituted phenyl. In one preferred embodiment, $R_2$, $R_3$, $R_4$, and $R_5$ are all methyl groups.

$R_6$ is a member selected from the group consisting of alkyl of 1 to 22 carbon atoms, alkenyl of 2 to 8 carbon atoms, phenyl substituted lower alkyl and lower alkyl substituted phenyl. As stated above, the essence of the $R_6$ group is that it must be functional to react with a free radical source to facilitate crosslinking of two or more polysiloxone backbones. Specific illustrations of $R_6$ groups are vinyl, octyl and p-tolyl.

It will be recognized that substitutions of any of the foregoing chemical groups for $R_1$-$R_7$ in Formula 3 will be within the scope of the present invention. By way of example only, substituting in one of these chemical groups for a hydrogen will be considered to be within the scope of the present invention. Thus, all well-known chemical substitutions or derivatives of the polymers of Formula 3 are to be considered within the scope of the present invention.

In Formula 3, d is an integer from 1 to about 14; e is an integer from 10 to about 40; f is an integer from 0 to about 1; and g is an integer from 3 to about 100. As stated above, depending on starting materials, the polymer elements d, e, and f used to form the polymer chain will be ordered in a statistically governed sequence. The specific sequence of these polymer elements has little or no effect in the functionality of the polymer. However, the percentages of d, e, and f in Formula 3 determine the percentage of chiral amide units on the polysiloxane chain. Thus, if e is 0 and f is only 0.5 to 2% of d, the polysiloxane chain will have nearly 50% of the chiral arylcarboxamide units. Compared to the numbers of d, f is normally very small. In one preferred embodiment, d=1, e=about 4, f=0 and $R_2$-$R_5$= methyl so that about 10% of the substituents on the silanes of the polymer are the chiral arylcarboxamide units.

Further, the degree of crosslinking during the formation of the polymer relates to the total number of alkyl (alkenyl) substituents, $R_2$, $R_3$, $R_4$, $R_5$, and $R_6$. In the most preferred embodiment of the present invention, polymers made in accordance with Formula 3 have 85-95% of the substituents as methyl groups (—$CH_3$).

The value of g in Formula 3 determines the degree of polymerization and thus the total number of chiral amide units in the polymer. In one presently preferred embodiment, g is about 5.

In the present most preferred embodiment, polymers made in accordance with Formula 3 have a g value within the range 3 to about 100 with the most preferred values for g being around 3 to 7. However, it will be appreciated that the precise value of g will depend on the particular application involved, with the optimum value of g depending on such factors as the desired efficiency and solubility of the resulting polysiloxane.

One compound embodied within the scope of Formula 3 has a=3, b=1, c=1, d=1, e=about 4, f=0, g=about 10, Aryl=phenyl, A=1-naphthyl, B=methyl, $R_1$ and $R_7$=methyl and $R_2$, $R_3$, and $R_4$=methyl ($R_5$ and $R_6$ are not present since f=0). In a second compound, a=3, b=1, c=1, d=1, e=about 4, f=0, g=10, Aryl=phenyl, A=phenyl, B=methyl, $R_1$ and $R_7$=methyl and $R_2$, $R_3$, and $R_4$=methyl ($R_5$ and $R_6$ are not present since f=0).

The preferred procedures to prepare the polymers in accordance with Formula 3 are in Procedure III below.

PROCEDURE III

In this procedure, the appropriate polyhydromethylsiloxane is first prepared. The polyhydromethylsiloxane itself is not part of this invention. The polysiloxane containing the chiral arylcarboxamide unit is part of the invention and is best made by reacting the chiral arylcarboxamide-containing alkene in Procedure I with a polyhydromethylsiloxane. The preparation of the polyhydromethylsiloxane is here reported.

In this regard, the appropriate mixture of 1,3,5,7-tetramethylcyclotetrasiloxane (D'4) and octamethylcyclotetrasiloxane (D4) along with a trace amount of hexamethyldisiloxane (to effect endcapping) are treated with an appropriate acid such as trifluoromethane sulfonic acid (triflic acid) for about 1 day at room temperature. It is to be recognized that the relative amounts of D'4 and D4 will determine the final ratio of d and e in the polymers of Formula 3. If the polymer made in accordance to Formula 3 needs to have about 10% of the chiral amide side group, the ratio of D'4 to D4 will be about 1 to 4. It is also recognized that where equimolar amounts of D'4 and D4 are used, the values of d and e in the final polymers made in accordance with Formula 3 will be approximately equal. After the above mixture of D'4, D4, hexamethyldisiloxane and acid are reacted, the mixture is neutralized using an appropriate base such as sodium bicarbonate or hexamethyldisilazane. The resulting polymer is dissolved in a minimum amount of $CH_2Cl_2$ (usually about 10 mL per gram of polymer) and precipitated with methanol (usually one to three times the amount of $CH_2Cl_2$). The mixture is centrifuged, the solvents are decanted and the precipitate is again dissolved in $CH_2Cl_2$. This process of dissolution in $CH_2Cl_2$ and precipitation with methanol is repeated 3 or 4 more times. The resulting polymer is dried under reduced pressure before being used in the next step.

In the second step of Procedure III, the chiral amide-substituted alkenes prepared in Procedure I above are attached to the polyhydromethylsilaxane made in the first step of Procedure III. The alkene of Procedure I can be purified to remove any alcohol or carbonyl functions by passing it through activated charcoal and alumina using a purified nonalcoholic solvent such as benzene as eluant. The alkene within the scope of Formula 1 and the polymer are mixed with the reactants being combined with about 1.1 to 1.5 equivalents of the alkene for each Si-H in the polymer. Small amounts (usually about 2 or 3% of the combined values of d and e in Formula 3) of 1-octene can also be added to the mixture to make the polymer in accordance with Formula 3 where $R_6$ is an octyl group. Only small amounts of octyl are needed for crosslinking purposes. To the mixture of these reactants is added enough benzene or toluene to dissolve the reactants and a catalytic amount of chloroplatinic acid (about 0.1M) in 1 part ethanol and 98 parts THF. The resulting mixture is heated to a temperature range of about 75° C. to about 90° C. for a period of about 2 hours to about 24 hours until the reaction is completed. Ethylene may be bubbled through the mixture to insure that all the Si-H groups have been reacted.

The polymer thus produced is precipitated by adding an equal volume of methanol to the reaction mixture. The polymer is then purified by dissolving it in a minimal amount of pentane or $CH_2Cl_2$ and subsequently precipitating it with methanol. This process may be repeated two or more times in order to obtain better purity. The purified product is then dried at a temperature within a range of 30° C. to about 60° C. under a vacuum of about 0.1 torr to about 1 torr for a period of about 12 hours to about 24 hours.

The following examples are given to illustrate various polymers which have been made or may be made in accordance with Formula 3 of the present invention. These examples are illustrative only, and are not comprehensive of the many different polymers which can be made in accordance with this embodiment.

EXAMPLE 7

In this example, a polysiloxane gum within the scope of Formula 3 was made wherein $a=3$, $b=1$, $c=1$, $d=1$, $e=$about 4, $f=0$, $g=$about 10, Aryl=phenyl, $A=$1-naphthyl, $B=$methyl, and $R_1$ and $R_7=$methyl, $R_2$, $R_3$, and $R_4=$methyl ($R_5$ and $R_6$ are not present since $f=0$).

In this regard, an approximately 7% hydro-containing polyhydromethylsiloxane was prepared as follows. Octamethylcyclotetrasiloxane (D4) (Silar) (1.0 g, 3.4 mole) was combined with 0.12 g (0.48 mole) of 1,3,5,7-tetramethylcyclotetrasiloxane (D'4) in a Teflon vial under an argon atmosphere. The mixture was stirred and 3 µL of hexamethyldisiloxane and 3 mg of triflic acid were added. The resulting mixture was stirred under argon for 18 hours. The acid was neutralized with 10 mg of hexamethyldisilazane. The mixture was dissolved in 10 mL of pentane and the polymer was precipitated with 10 mL of methanol. This process was repeated 5 more times. The NMR spectrum of this polymer exhibited a band corresponding to about 7% of the Si-H hydrogens. A mixture of 750 mg of the polyhydromethylsiloxane, 1 mL of anhydrous benzene and 0.22 g (a 50% excess) of the compound made in Example 1 was stirred and heated at 85° C. under argon for 1 hour. Chloroplatinic acid hexahdrate catalyst (1% $H_2PtCl_6.6H_2O$ in a 1% ethanol-98% tetrahydrofuran solution) was added in two 15 -µL portions. The reaction was allowed to stir at 85° C. under argon for 36 hours. The reaction was cooled and a drop of mercury was added, and the material was stirred overnight to help remove the colloidal platinum. Five mL of methylene chloride were added and the solution was decanted away from the mercury. Methanol (about 30 mL) was added to the organic phase to precipitate the polymer. The process of dissolving the polymer in methylene chloride and precipitation with methanol was repeated four more times. The resulting polymer was dried overnight in a vacuum oven at 40° C. The NMR spectrum of this material showed no Si-H peak, but did show small peaks indicative of the amide substituent. The polymer had transition temperatures of k 97 s 116 i.

EXAMPLE 8

In this Example, a polysiloxane gum within the scope of Formula 3 was made wherein $a=3$, $b=1$, $c=1$, $d=1$, $e=$about 4, $f=0$, $g=$about 10, Aryl=phenyl, $A=$phenyl($—C_6H_5$), $B=$methyl ($—CH_3$), $R_1$ and $R_7=$methyl, $R_2$, $R_3$, and $R_4=$methyl ($R_5$ and $R_6$ are not present since $f=0$).

The polysiloxane of Example 8 was prepared exactly as the polymer of Example 7 except 0.22 g of the alkene of Example 2 was used in Example 8 rather than 0.22 g of the alkene of Example 1 which was used in Example 7. The resulting polymer was a gum.

UTILITY

The polymers of the present invention have shown utility in connection with stationary phases used in gas-liquid and supercritical fluid chromatography. One presently preferred procedure for applying the polymers of the present invention to a chromatographic column is given in Procedure IV below.

PROCEDURE IV

In this procedure, the polymer to serve as the stationary phase, is statically coated on fused silica capillary columns. The fused silica capillaries (for example, about 10–30 meter long and about 25–500 micrometers in inner diameter) are prepared for chromatographic analysis in accordance with the present invention as follows.

First, the fused silica capillaries are purged with dry nitrogen gas at about 250° C. for about two hours before use. The polymer is dissolved in methylene chloride or other low boiling solvent at about 35° C. at a sufficient concentration to provide a film thickness of about 0.05–10 micrometers by the static coating method. Before filling the fused silica capillaries, the coating solution is carefully filtered through a two-micrometer metal filter device. The columns are then coated with the polymer and purged with nitrogen gas for about 30 minutes to remove all traces of solvent. The coating or stationary phase thus applied to the fused silica capillaries is next preferably crosslinked using azo-t-butane as free radical initiator.

To achieve such crosslinking, the coated columns are purged with azo-t-butane saturated argon gas. The column ends are then sealed, and the columns are heated from about 40° C. to about 220° C. by increasing the temperature at the rate of about 4° C. per minute, and holding at the final temperature of about 220° C. for about 30–40 minutes. After crosslinking, the column is purged with dry nitrogen gas at room temperature to remove excess azo-t-butane and reaction by-products. Such a crosslinking procedure provides crosslinkages between the methyl, ethyl, octyl and/or methylene functional groups in the polymer. Of course, it will be recognized that other free radical initiators can be used instead of azo-t-butane and that the crosslinking reaction can be performed statically in a sealed column as set forth in this procedure, or dynamically where the column is purged with an inert gas during the reaction.

The following examples are given to illustrate the various silica columns for gas-liquid and supercritical fluid chromatography, and silica particles for liquid chromatography which can be coated with materials made in accordance with Formula 3 of the present invention. These examples are exemplary only, and are not comprehensive of the many different coatings that can be made in accordance with the present invention.

EXAMPLE 9

In this example, the polymer of Example 7 (made from the alkene of Example 1) was applied as a stationary phase in a gas-liquid chromatographic column. A fused silica capillary column, about 20 meter long and about 0.2 millimeters in inner diameter (supplied by Polymicro Technologies, Phoenix, Arizona) was purged with nitrogen gas at 250° C. for 2 hours. The capillary was then statically coated at room temperature using 0.5% (w/v) stationary phase solutions in methylene chloride or Freon 21, which were previously filtered through a 0.2 -μm Millipore filter. The film thickness of the phase was approximately 0.25 μm. The column was tested for efficiency, selectivity, and thermal stability before being crosslinked. The column was crosslinked by purging with azo-t-butane vapors in nitrogen gas at room temperature for 1 hour at a flow rate of 3 mL min$^{-1}$. Both ends of the column were sealed, and the column was heated from 40° C. to 220° C. at 4° C. min$^{-1}$ and held at 220° C. for 40 min. The column was then rinsed with 2 mL of methylene chloride and reconditioned at 280° C. for 10 hours.

EXAMPLE 10

In this example, the polymer of Example 8 (made from the alkene of Example 2) was applied as a stationary phase to a gas-liquid chromatographic column in accordance with the procedure of Example 9.

EXAMPLE 11

In this example, the polymer of Example 7 was applied as a stationary phase in a supercritical fluid capillary column. A fused silica column about 10 meters long and about 0.05 to 0.005 millimeters in inner diameter (supplied by Polymicro Technologies, Phoenix, Arizona) was statically coated with about 0.15 micrometer film of the polymer as in Example 9.

EXAMPLE 12

In this example, the chiral amide-containing the triethoxysilane of Example 6 in chloroform was mixed with silica gel particles in a ratio of 1 part diethoxysilane of Example 6 to 10 parts silica gel. The chloroform was removed under vacuum on a rotary evaporator to insure a reasonable uniform coating of the diethoxysilane of Example 6 in the silica gel. The gel was then heated at 250° C. for 10 to 20 hours. The resulting material was suitable for use as an LC packing.

Crosslinking of the polymeric stationary phase within the column helps to prevent washout of the polymer after repeated use. Additionally, the stationary phase of the present invention can be used in supercritical fluid chromatography where even higher demands are put on the crosslinked polymers. Such crosslinked polymers have been found to withstand the strong solubilizing properties of supercritical fluids. Thus, the present invention has found particular utility in supercritical fluid chromatography applications.

The polymer coated column of Examples 9 and 10 have been chromatographically tested for gas-liquid chromatography and have shown utility in separating various organic enantiomeric mixtures. The separation performance of the polymer phases of the present invention were compared with the performance of Chirasil-val ™, the standard chiral phase used for gas chromatographic separations.

In FIGS. 1-4 of the present application, several gas-liquid chromatograms are illustrated showing the separation achieved when two polymers of the present invention are used as stationary phases. In each of the gas-liquid chromatograms illustrated in FIGS. 1-4, a Carlo Erba 5160 Mega Series gas chromatograph equipped with a flame ionization detector was used. A Lee Scientific SFC instrument was used to record the SFC chromatogram illustrated in FIG. 5. Hydrogen gas at 50-100 cm s$^{-1}$ was used as the carrier gas.

The α values (a measure of the separation of two enantiomers) determined for the new phase of Example 7 was similar to the α values found in the literature for Chirasil-val ™. This shows that enantiomeric separations by the new phases of the present invention are in the same selectivity range as the most frequently used chiral phase. The new phases of Examples 7 and 8 are usable to a temperature of about 280° C. while Chirasil-val ™ cannot be used above about 220° C. and the new phases are crosslinkable, and they can be synthesized in a reproducible way.

Figure 2:
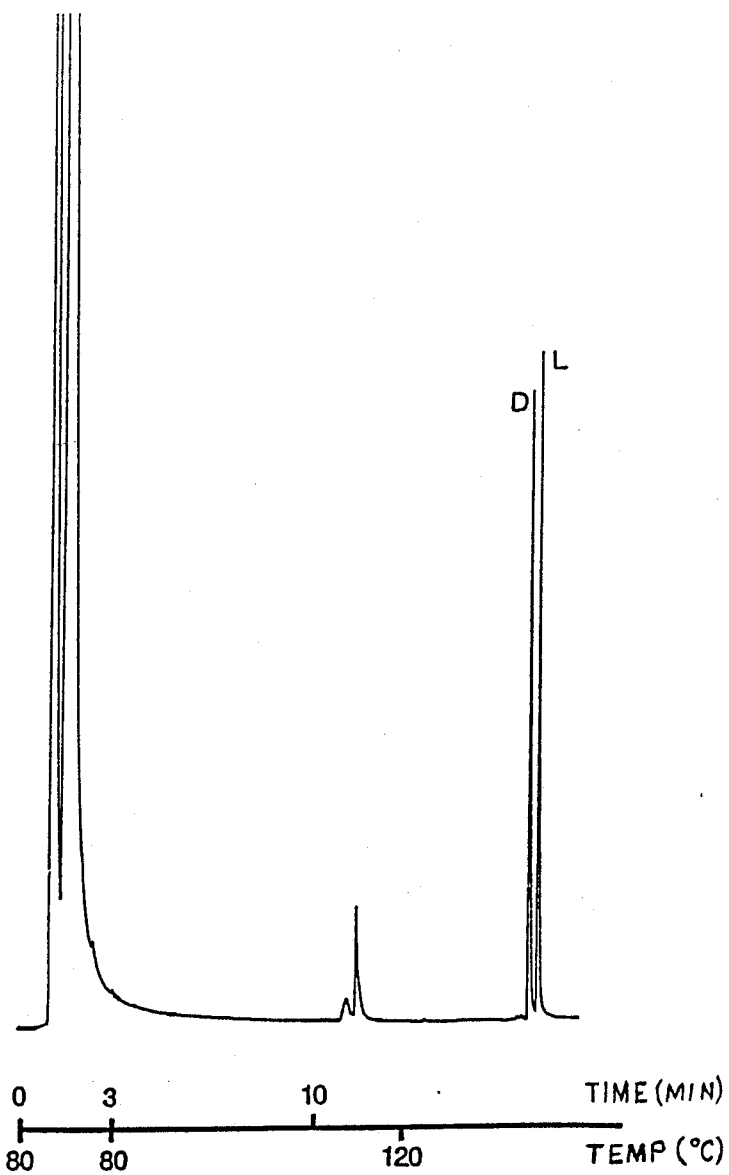
FIG. 2 illustrates a gas-liquid chromatogram wherein derivatives of the D and L isomers of valine were separated, using the same stationary phase as in FIG. 1.
Figure 3:
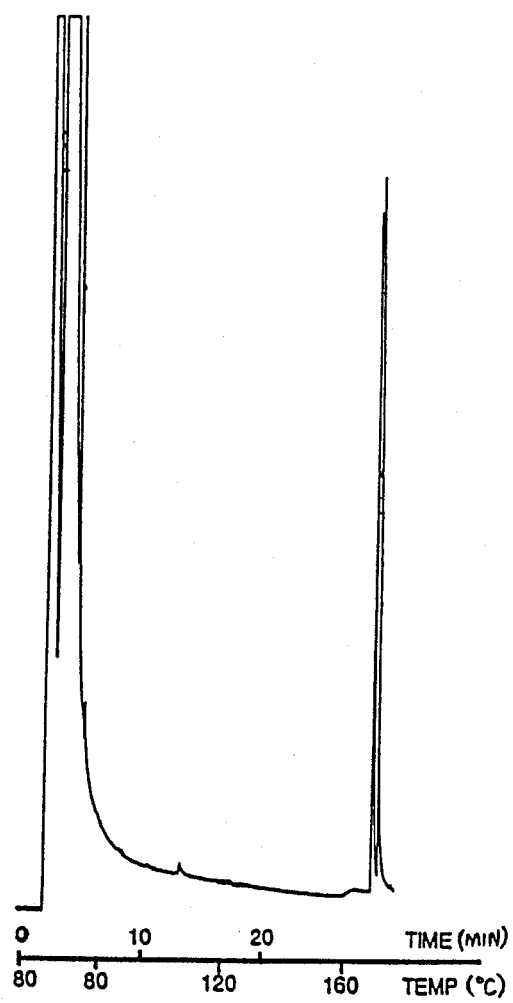
FIG. 3 illustrates a gas-liquid chromatogram wherein derivatives of the D and L isomers of alanine were separated using a stationary phase made in accordance with the same embodiment of the present invention.
Figure 4:
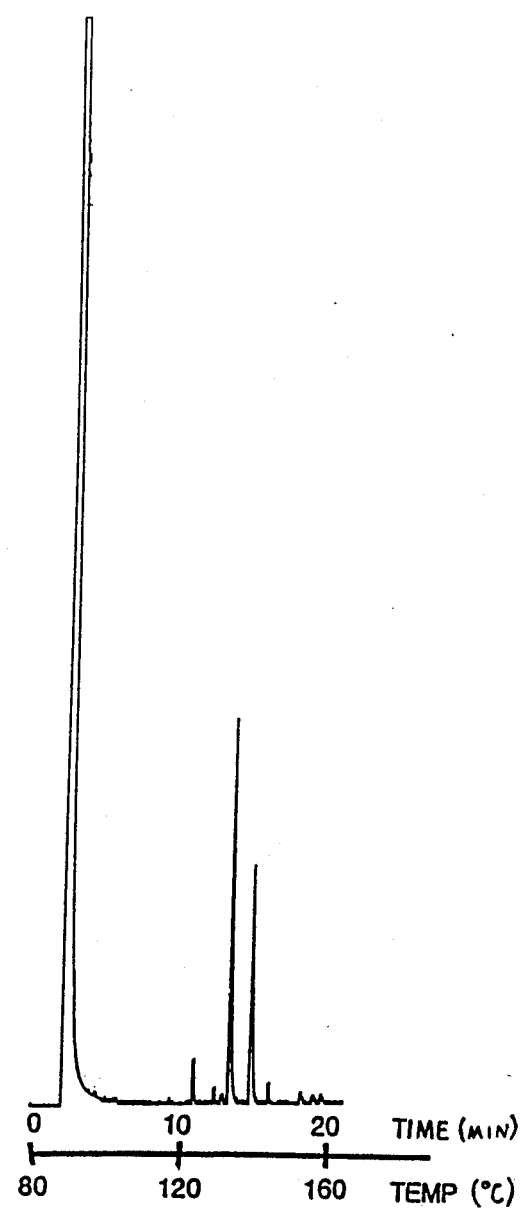
FIG. 4 illustrates a chromatogram wherein the stereoisomers of trans-verbinol, a known pheromone material, were separated using a stationary phase made in accordance with the same embodiment of the present invention.
Figure 5:
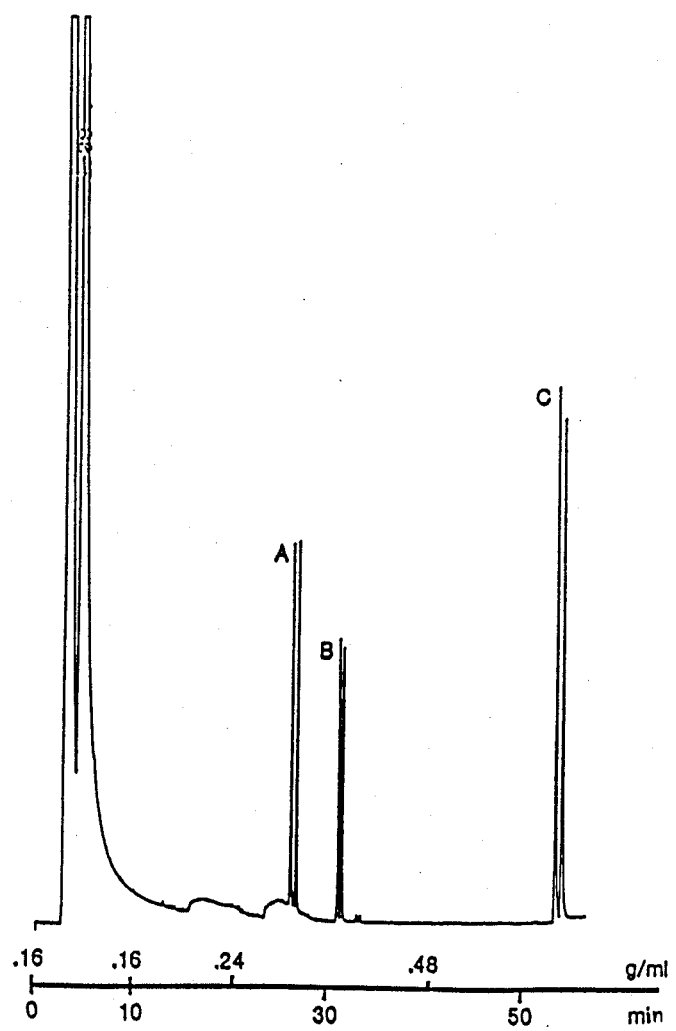
FIG. 5 illustrates a chromatogram wherein various derivatives of the D and L isomers of proline were separated on a supercritical fluid chromatograph using a stationary phase in accordance with one embodiment of the present invention.

The new chiral amide phase of Example 7 of the present invention has utility in the separation of enantiomeric mixtures of various organic substances. This fact is shown in FIGS. 1-5. In FIG. 1, the separation of the N-pentafluoropropionyl-O-isopropyl ester derivatives of D and L isomers of methionine using the phase of Example 7 in gas-liquid chromatography are illustrated. The separation of the N-acetyl derivatives of D and L isomers of valine using the phase of Example 7 in gas-liquid chromatography is shown in FIG. 2. FIG. 3 illustrates the chromatogram showing the separation of the N-acetyl derivatives D and L isomers of alanine using the phase of Example 7 in gas-liquid chromatography. The separation of the stereoisomers of the pheromone trans-verbinol in gas-liquid chromatography using the phase of Example 7 is illustrated in FIG. 4. The separation of (A) the N-pentafluoropropionyl-O-methyl ester derivatives, (B) the N-pentafluoropropionyl-O-isopropyl ester derivatives and (C) the N-acetyl derivatives of the D and L-isomers of proline in SFC using supercritical $CO_2$ is shown in FIG. 5.

From the foregoing, it will be appreciated that the polymers of the present invention provide stationary phases which are superior to the presently used chiral phases in that they provide similar separations of the enantiomers of many organic compounds but that the phases are operational at higher temperatures (up to 280° C.). Further, the polymers of the present invention are suitable for use as stationary phases in SFC. In addition, the compounds of Formula 2 can be used to prepare chiral arylcarboxamide-containing silica particles for LC and packed column SFC use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letter Patent is:

1. A compound useful for chromatographic separations of formula

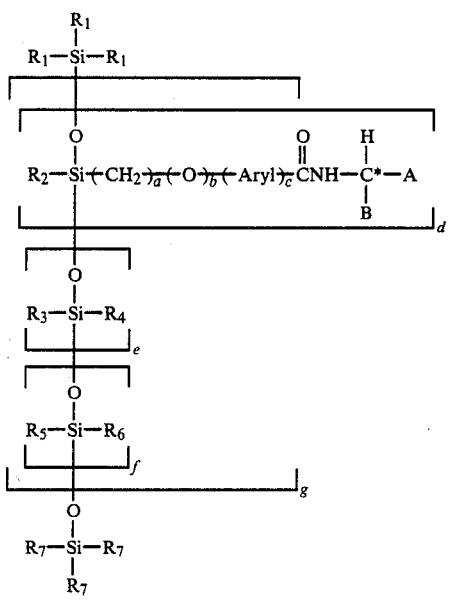

wherein;
a is an integer from 2 to about 14; b is an integer of 0 or 1; c is an integer of 0 or 1; d is an integer from 1 to about 4; e is an integer from 10 to about 40; f is an integer of 0 or 1; and g is an integer from 3 to about 100;

Aryl is phenyl or naphthyl or their nitrogen-containing analogs; A is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl, any alkoxy- or aryloxycarbonyl group ($-CO_2R^1$) where $R^1$ is any alkyl of 1 to 22 carbons or phenyl, naphthyl or biphenyl; any mono- or disubstituted carboxamide group [$C(O)NR^2R^3$] where $R^2$ is any alkyl of 1 to 22 carbons or phenyl, naphthyl or biphenyl or any alkyl ester of an amino acid unit such as alanine or phenylalanine (the nitrogen atom of the carboxamide group would be the nitrogen atom of the amine group of the amino acid, alkyl ester), any alkyl ester of a di- or tripeptide (the nitrogen atom of the carboxamide group would be one of the nitrogen atoms of the amine groups of the di- or tripeptide), a phenyl or methylene unit substituted with any lower oligoethyleneoxy unit ending with a methoxy or ethoxy group or substitutions of any of the foregoing and $R^3$ is hydrogen, any alkyl of 1 to 8 carbon atoms or phenyl; B is any alkyl of 1 to 22 carbons, aryl selected from the group consisting of phenyl, naphthyl and biphenyl or their nitrogen containing analogs, and pyridyl and furyl and the lower alkyl, lower alkoxy, lower alkoxycarbonyl and lower alkylamido substituents thereof; lower aralkyl; and * indicates that the carbon is chiral;

$R_1$ and $R_7$ are selected from the group consisting of lower alkyl, lower alkenyl, lower haloalkyl and phenyl;

$R_2$, $R_3$, $R_4$, and $R_5$ are members selected from the group consisting of hydrogen, lower alkyl, phenyl, phenyl substituted lower alkyl, lower alkyl substituted phenyl, lower alkoxy substituted phenyl and halosubstituted phenyl;

$R_6$ is a member selected from the group consisting of alkyl of 1 to 12 carbon atoms, alkenyl of 2 to 8 carbon atoms, phenyl substituted lower alkyl and lower alkyl substituted phenyl.

2. A compound as defined in claim 1 wherein a=3, b=1 and c=1.

3. A compound as defined in claim 1 wherein a=2, b=0 and c=1.

4. A compound as defined in claim 1 wherein d=4 and e=10 to about 25.

5. A compound as defined in claim 1 wherein d=10 and e=10.

6. A compound as defined in claim 1 wherein f=0.

7. A compound as defined in claim 1 wherein g is an integer from 3 to about 20.

8. A compound as defined in claim 1 wherein Aryl is phenyl ($-C_6H_5$), A is 1-naphthyl ($1-C_{10}H_7$) and B is methyl.

9. A compound as defined in claim 1 wherein Aryl is phenyl ($-C_6H_5$), A is phenyl ($-C_6H_5$) and B is methyl.

10. A compound as defined in claim 1 wherein Aryl is phenyl ($-C_6H_5$), A is isopropoxycarbonyl [$-CO_2CH(CH_3)_2$] and B is sec-butyl [$-CH(CH_3)CH_2CH_3$].

11. A compound as defined in claim 1 wherein Aryl is phenyl ($-C_6H_5$), A is 4-methoxyphenoxy-carbonyl ($-CO_2-4-C_6H_4OCH_3$) and B is methyl ($-CH_3$).

12. A compound as defined in claim 1 wherein $R_1$ and $R_7$ are both methyl ($-CH_3$).

13. A compound as defined in claim 1 wherein $R_2$, $R_3$, $R_4$ and $R_5$ are all methyl ($-CH_3$).

14. A compound as defined in claim 1 wherein a=3, b=1, c=1, d=1, e=about 4, f=0, g=10, Aryl=phenyl ($-C_6H_5$), A=1-naphthyl ($1-C_{10}H_7$), B=methyl ($-CH_3$), $R_1$ and $R_7$=methyl ($-CH_3$), $R_2$, $R_3$ and $R_4$=methyl ($-CH_3$) ($R_5$ and $R_6$ are not present since f=0).

15. A compound as defined in claim 1 wherein a=3, b=1, c=1, d=1, e=about 4, f=0, g=about 10, Aryl=phenyl ($-C_6H_5$), A=phenyl ($-C_6H_5$), B=methyl ($-CH_3$), $R_1$ and $R_7$=methyl ($CH_3$), $R_2$, $R_3$ and $R_4$=methyl ($-CH_3$) ($R_4$ and $R_5$ are not present since f=0).

* * * * *